United States Patent
Luebke et al.

(10) Patent No.: US 10,167,241 B2
(45) Date of Patent: Jan. 1, 2019

(54) TWO-BED PARAFFIN TO OLEFIN ENHANCEMENT PROCESS

(71) Applicant: UOP LLC, Des Plaines, IL (US)

(72) Inventors: Charles P. Luebke, Mount Prospect, IL (US); Zheng Wang, Villa Park, IL (US); Jayant K. Gorawara, Buffalo Grove, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/987,839

(22) Filed: May 23, 2018

(65) Prior Publication Data

US 2018/0265432 A1    Sep. 20, 2018

Related U.S. Application Data

(63) Continuation of application No. PCT/US2016/062147, filed on Dec. 2, 2016.

(60) Provisional application No. 62/264,040, filed on Dec. 7, 2015.

(51) Int. Cl.
| | |
|---|---|
| *C07C 7/12* | (2006.01) |
| *B01D 15/18* | (2006.01) |
| *C10G 25/00* | (2006.01) |
| *C10G 29/20* | (2006.01) |
| *C10G 53/08* | (2006.01) |

(Continued)

(52) U.S. Cl.
CPC ............ *C07C 7/12* (2013.01); *B01D 15/1814* (2013.01); *B01D 15/1864* (2013.01); *B01D 53/0423* (2013.01); *C07C 2/66* (2013.01); *C10G 25/00* (2013.01); *C10G 29/205* (2013.01); *C10G 53/08* (2013.01); *B01D 2256/24* (2013.01); *B01D 2257/7027* (2013.01); *B01D 2259/402* (2013.01); *B01D 2259/40092* (2013.01)

(58) Field of Classification Search
CPC ........................................................ C07C 7/12
USPC .................................. 585/825, 826, 827, 831
See application file for complete search history.

(56) References Cited

U.S. PATENT DOCUMENTS

| | | |
|---|---|---|
| 5,276,231 A | 1/1994 | Kocal et al. |
| 6,407,305 B1 | 6/2002 | Sohn et al. |
| 6,417,420 B1 | 7/2002 | Stewart et al. |

(Continued)

FOREIGN PATENT DOCUMENTS

| | | |
|---|---|---|
| EP | 0422421 A1 | 4/1991 |
| WO | 1994002573 A1 | 2/1994 |
| WO | 9815608 A2 | 4/1998 |

OTHER PUBLICATIONS

Faghihian, H. et al., "Dearomatization of normal paraffin by adsorption process using synthesized NaX zeolite", Petroleum Science, v 10, n 3, p. 408-14, Sep. 2013.

(Continued)

*Primary Examiner* — Thuan D Dang

(57) ABSTRACT

A process is presented for the purification of an olefins feed stream to a benzene alkylation unit. The process removes heavy aromatics in a two adsorbent unit system. The unit passes the olefins feed stream to a first adsorbent unit, while the second adsorbent unit is either in regeneration mode, or standby mode. The process switches the feed stream to the second adsorbent unit and displaces the fluid in the second adsorbent unit, while maintaining the flow of the purified feed stream to the benzene alkylation unit.

5 Claims, 1 Drawing Sheet

(51) Int. Cl.
*B01D 53/04* (2006.01)
*C07C 2/66* (2006.01)

(56) References Cited

U.S. PATENT DOCUMENTS

| | | |
|---|---|---|
| 6,670,519 B1 | 12/2003 | Sohn et al. |
| 7,576,247 B2 | 8/2009 | Sohn et al. |
| 2008/0161627 A1* | 7/2008 | Glover .................... C07C 2/66 585/807 |

OTHER PUBLICATIONS

King, S. et al., "Naphtha normal paraffin separation using a dividing wall column and simulated moving adsorption bed", 11 AIChE—2011 AIChE Spring Meeting and 7th Global Congress on Process Safety, Conference Proceedings, p. 1P, 2011, 11 AIChE—2011 AIChE Spring Meeting and 7th Global Congress on Process Safety, Conference Proceedings.

Urbanczyk, S. et al., "Adsorption process for dearomatizing kerosine fractions to prepare synthetic detergents", 35th Ind Chem Intern Congr (Warsaw Sep. 19, 1964) Erdoel Kohle V19 N.5.351-54 (May 1966), Sep. 19, 1964.

Kasatkin, Osnovnye Protsesy I Apparaty Khimicheskoi Thekhologii, 1961, pp. 531-532. Language: Russian.

PCT Search Report dated Feb. 9, 2017 for corresponding PCT Application No. PCT/US2016/062147.

\* cited by examiner

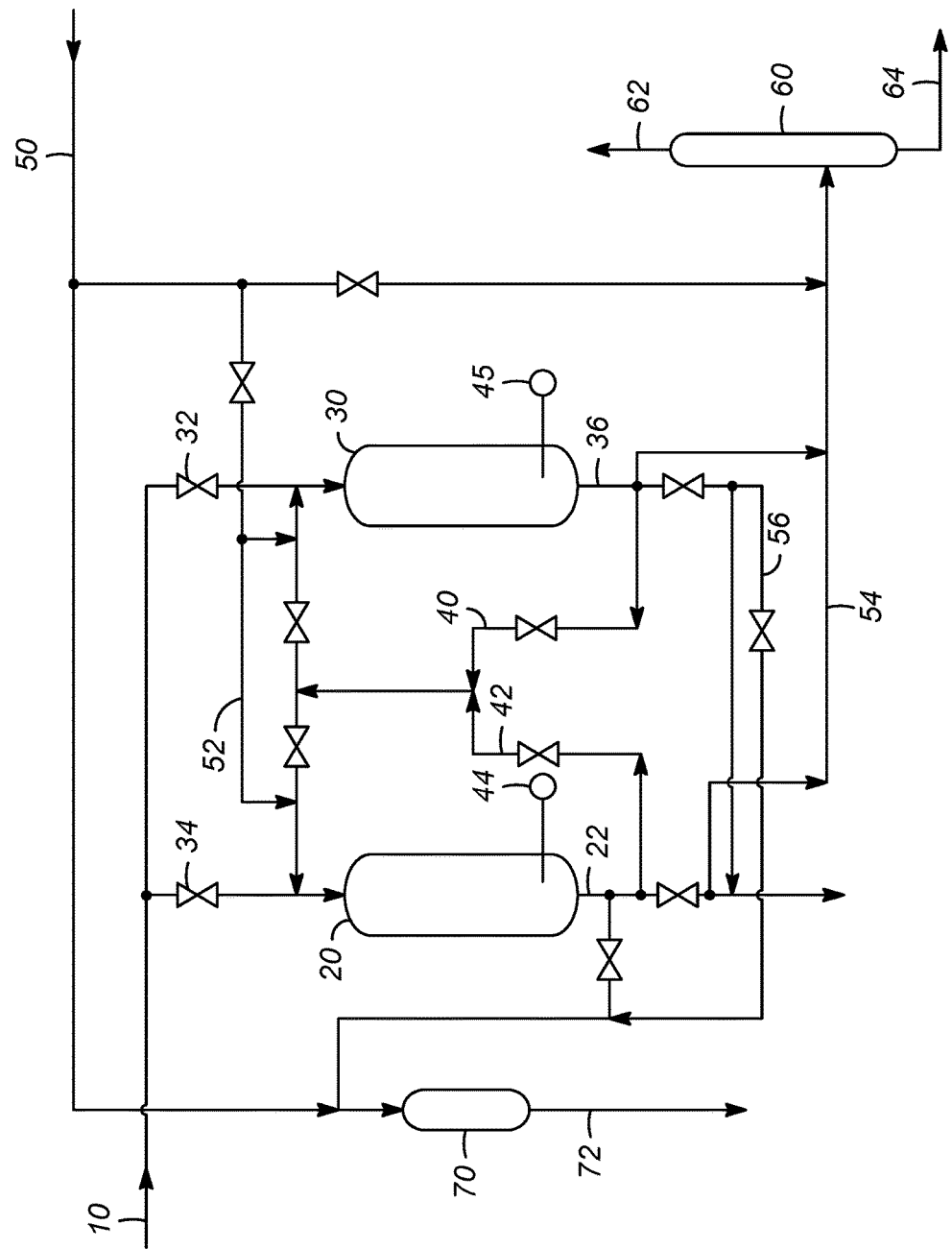

TWO-BED PARAFFIN TO OLEFIN ENHANCEMENT PROCESS

CROSS-REFERENCE TO RELATED APPLICATIONS

This application is a Continuation of copending International Application No. PCT/US2016/062147 filed Dec. 2, 2016, which application claims priority from U.S. Provisional Application No. 62/264,040 filed Dec. 7, 2015, the contents of which cited applications are hereby incorporated by reference in their entirety.

FIELD OF THE INVENTION

The present invention is related to a process for producing a purified feed to a benzene alkylation unit by removing heavy aromatics.

BACKGROUND

The production of normal paraffins provides the ability of upgrading products from straight runs of hydrocarbon streams derived from crude oil fractionation. In particular, straight run kerosene is further processed to separate out normal paraffins for higher valued products, such as used in the production of linear alkyl benzenes (LAB). Normal paraffins in the range of C10 to C13 are important precursors to LAB production, which is in turn used to produce linear alkyl benzene sulfonate (LAS). LAS is the predominant surfactant used in the production of detergents.

The large utility of detergents and other cleaners has led to extensive development in the areas of detergent production and formulation. While detergents can be formulated from a wide variety of different compounds much of the world's supply is formulated from chemicals derived from alkylbenzenes. The compounds are produced in petrochemical complexes in which an aromatic hydrocarbon, typically benzene, is alkylated with an olefin of the desired structure and carbon number for the side chain. Typically the olefin is actually a mixture of different olefins forming a homologous series having a range of three to five carbon numbers. The olefin(s) can be derived from several alternative sources. For instance, they can be derived from the oligomerization of propylene or butenes or from the polymerization of ethylene. Economics has led to the production of olefins by the dehydrogenation of the corresponding paraffin being the preferred route to produce the olefin.

The choice of carbon numbers is set by the boiling point range of straight run cuts from crude distillation. Kerosene boiling range fractions from crude oil provide heavier paraffins. Paraffins having 8 to 15 carbons are present in significant concentrations in relatively low cost kerosene. These paraffins have been a predominant source for linear alkanes and the leading source of olefin precursors for use in making LABs. Recovery of the desired normal paraffins from kerosene is performed by adsorption separation, which is one process in overall production of LABs. The paraffins are then passed through a catalytic dehydrogenation zone wherein some of the paraffins are converted to olefins. The resultant mixture of paraffins and olefins is then passed into an alkylation zone in which the olefins are reacted with the aromatic substrate. This overall flow is shown in U.S. Pat. No. 5,276,231, which is incorporated by reference in its entirety, directed to an improvement related to the adsorptive separation of byproduct aromatic hydrocarbons from the dehydrogenation zone effluent. PCT International Publication WO 99/07656 indicates that paraffins used in this overall process may be recovered through the use of two adsorptive separation zones in series, with one zone producing normal paraffins and another producing monomethyl paraffins.

While adsorption separation technology allows for the separation of normal paraffins from a hydrocarbon mixture, there are problems in recovering higher molecular weight paraffins after the separation that currently limit the ability to recover higher molecular weight normal paraffins.

SUMMARY

The present invention relates to an improved process for the removal of heavy aromatics from an olefins stream to generate a high quality feed stream for a detergent alkylation unit.

A first embodiment of the invention is a process for the removal of heavy aromatics from an olefins stream comprising passing an olefins feed stream to a first adsorbent unit in two unit adsorbent system to generate a first adsorbent effluent stream with reduced heavy aromatics content; running the first adsorbent unit until breakthrough; equalize pressure in a second adsorbent unit to the pressure of the first adsorbent unit; pass the olefins feed stream to the second adsorbent unit to generate a second adsorbent unit effluent stream with reduced heavy aromatics content; pass the second adsorbent unit effluent stream to the first adsorbent unit, displacing the first adsorbent unit fluid; discontinue the first adsorbent unit displacement; pass regenerant to the first adsorbent unit to regenerate the first adsorbent unit, wherein the regenerant flows in a co-current direction relative to the olefin feed stream through the first adsorbent unit; equalize the in the first adsorbent unit to the pressure of the second adsorbent unit; pass the olefins feed stream to the first adsorbent unit to generate the first adsorbent unit effluent stream; pass the first adsorbent unit effluent stream to the second adsorbent unit, displacing the second adsorbent unit fluid; discontinue the second adsorbent unit displacement; and pass regenerant to the second adsorbent unit to regenerate the second adsorbent unit, wherein the regenerant flows in a co-current direction relative to the olefin feed stream through the first adsorbent unit. An embodiment of the invention is one, any or all of prior embodiments in this paragraph up through the first embodiment in this paragraph further comprising passing the first adsorbent bed effluent stream to a benzene alkylation unit. An embodiment of the invention is one, any or all of prior embodiments in this paragraph up through the first embodiment in this paragraph further comprising passing the second adsorbent bed effluent stream to a benzene alkylation unit. An embodiment of the invention is one, any or all of prior embodiments in this paragraph up through the first embodiment in this paragraph further comprising a trim displacement of the first adsorption unit following the first adsorption unit displacement. An embodiment of the invention is one, any or all of prior embodiments in this paragraph up through the first embodiment in this paragraph wherein the trim displacement is performed with regenerant. An embodiment of the invention is one, any or all of prior embodiments in this paragraph up through the first embodiment in this paragraph further comprising a trim displacement of the second adsorption unit following the second adsorption unit displacement. An embodiment of the invention is one, any or all of prior embodiments in this paragraph up through the first embodiment in this paragraph wherein the trim displacement is performed with regenerant. An embodiment of the invention is one, any or all of prior embodiments in this paragraph up through the first embodiment in this paragraph further comprising putting the first adsorbent unit on standby after passing the regenerant to the first adsorbent unit. An embodiment of the invention is one, any or all of prior embodiments in this paragraph up through the first embodiment in this paragraph further comprising putting the second adsorbent unit on standby after passing the regenerant to the second adsorbent unit. An embodiment of the invention is one, any or all of prior embodiments in this paragraph up through the first embodiment in this paragraph wherein the regenerant is benzene. An embodiment of the invention is one, any or all of prior embodiments in this paragraph up through the first embodiment in this paragraph wherein the heavy aromatics comprise C7 and heavier aromatics. An embodiment of the invention is one, any or all of prior embodiments in this paragraph up through the first embodiment in this paragraph wherein the olefins feed stream is generated by a paraffins dehydrogenation unit. An embodiment of the invention is one, any or all of prior embodiments in this paragraph up through the first embodiment in this paragraph further comprising passing the first adsorbent unit effluent stream to an alkylation unit. An embodiment of the invention is one, any or all of prior embodiments in this paragraph up through the first embodiment in this paragraph further comprising passing the second adsorbent unit effluent stream to an alkylation unit. An embodiment of the invention is one, any or all of prior embodiments in this paragraph up through the first embodiment in this paragraph wherein the alkylation unit is a benzene alkylation unit.

A second embodiment of the invention is a process for the removal of heavy aromatics from an olefins stream comprising passing an olefins feed stream to a first adsorbent unit in two unit adsorbent system to generate a first adsorbent effluent stream with reduced heavy aromatics content; running the first adsorbent unit until breakthrough; equalize pressure in a second adsorbent unit to the pressure of the first adsorbent unit; pass the olefins feed stream to the second adsorbent unit to generate a second adsorbent unit effluent stream with reduced heavy aromatics content; pass the second adsorbent unit effluent stream to the first adsorbent unit, displacing the first adsorbent unit fluid; discontinue the first adsorbent unit displacement and moving the first adsorbent unit off-line and the second adsorbent unit on-line; performing a trim displacement of the first adsorption unit following the first adsorption unit displacement; pass regenerant to the first adsorbent unit to regenerate the first adsorbent unit, wherein the regenerant flows in a co-current direction relative to the olefin feed stream through the first adsorbent unit; equalize the in the first adsorbent unit to the pressure of the second adsorbent unit; pass the olefins feed stream to the first adsorbent unit to generate the first adsorbent unit effluent stream; pass the first adsorbent unit effluent stream to the second adsorbent unit, displacing the second adsorbent unit fluid; discontinue the second adsorbent unit displacement and moving the second adsorbent unit off-line and the first adsorbent unit on-line; performing a trim displacement of the second adsorption unit following the second adsorption unit displacement; and pass regenerant to the second adsorbent unit to regenerate the second adsorbent unit, wherein the regenerant flows in a co-current direction relative to the olefin feed stream through the first adsorbent unit. An embodiment of the invention is one, any or all of prior embodiments in this paragraph up through the second embodiment in this paragraph further comprising passing the first adsorbent unit effluent stream and the second adsorbent unit effluent stream to an alkylation unit.

An embodiment of the invention is one, any or all of prior embodiments in this paragraph up through the second embodiment in this paragraph wherein the regenerant is benzene. An embodiment of the invention is one, any or all of prior embodiments in this paragraph up through the second embodiment in this paragraph wherein the heavy aromatics comprise C7 and heavier aromatics. An embodiment of the invention is one, any or all of prior embodiments in this paragraph up through the second embodiment in this paragraph wherein the trim displacement comprises passing benzene to the adsorbent unit being moved off line.

Other objects, advantages and applications of the present invention will become apparent to those skilled in the art from the following detailed description and drawing.

BRIEF DESCRIPTION OF THE DRAWING

The FIGURE presents the layout and flow scheme for a two bed system.

DETAILED DESCRIPTION

Olefins for use in the production of linear alkylbenzenes (LABs) are generated by dehydrogenation of paraffins to produce an olefins feed stream. The paraffin dehydrogenation process for the production of olefins generates aromatics. The aromatics include heavy aromatics that comprise aromatics with 7 or more carbons. The heavy aromatics are impurities that affect the quality of the LAB product and need to be removed before the alkylation step. A current design is complex and expensive, and utilizes a six bed adsorption system. The system includes a separate displacement liquid and requires a divided wall column for the separation of the displacement liquid, the regenerate, and the heavy aromatics.

Currently, the process for the removal of heavy aromatics from an olefin feed stream, before passing the olefin feed stream to an alkylation unit, is a complex unit. The heavy aromatics removal process utilizes six adsorbers with four on-line in a parallel configuration. The other two adsorbers are in various stages of regeneration or displacement, with displacement using n-pentane. The spent regenerant, which is benzene, and the n-pentane are sent to respective mix drums. The effluent from each of these mix drums are sent to a regenerant column as separate feeds. The regenerant column is a divided wall column and essentially results in an overhead n-pentane stream which is recycled back as displacement liquid, a side desorbent liquid which is sent to the alkylation unit, and the bottoms heavy aromatic product.

The improved heavy aromatics removal design only requires two beds and does not require a separate displacement purge step. Since the displacement liquid is no longer required, the regenerant column design is simplified. The column does not need to be a divided wall column since only a benzene overhead stream and heavy aromatic bottoms product is required. The new design will remove at least 80% of the heavy aromatics from the feed, and maximize the recovery of the olefins feed stream for passing to a benzene alkylation unit. The new design also provides for a continuous flow of feed to the alkylation unit and a continuous flow of spent regenerant to the regenerant column.

The present invention provides a method to reduce the cost and utilities of the present process for the removal of heavy aromatics. The improved design also reduces the complexity of the unit, the cost of the unit and will reduce the utilities since no separate displacement liquid is used.

The present invention is a process for the removal of heavy aromatics from the olefin feedstream to a benzene alkylation unit. The process utilizes a two bed system without the need for a separate displacement liquid, and without the need for the divided wall column. The process includes passing an olefins feed stream to a first adsorbent unit, in a two unit adsorbent system, and generates a first adsorbent effluent stream with reduced heavy aromatics content. The first adsorbent unit effluent stream with reduced heavy aromatics is passed to a benzene alkylation unit. The first adsorbent bed is run until breakthrough. At breakthrough, the pressure of a second adsorbent unit is equalized with the pressure of the first adsorbent unit. The olefins feed stream is switched from the first adsorbent unit to the second adsorbent unit to generate a second adsorbent bed effluent stream.

Breakthrough is determined by an analyzer disposed within the adsorbent beds to determine when the heavy aromatics content is exceeding a preset level. The analyzer is positioned before the end of the adsorbent bed, such that there is sufficient adsorbent in the bed to prevent the level of heavy aromatics from exceeding the preset level, when breakthrough is achieved. The equalization of the pressure can be set at the inlet of each adsorbent bed.

The second adsorbent bed effluent stream initially comprises the displacement fluid in the second adsorbent bed. The second adsorbent unit effluent stream is passed to the first adsorbent unit, displacing the residual first adsorbent unit fluid. Upon displacing the residual first adsorbent unit fluid, the displacement of the first adsorbent unit is discontinued, and the second adsorbent bed effluent stream is now on-line. The second adsorbent bed effluent stream is passed to the benzene alkylation unit. A regenerant is passed to the first adsorbent unit to regenerate the first adsorbent unit. The regenerated flows in the same direction through the first adsorbent unit as the olefins feed stream. When the first adsorbent unit is regenerated it is placed on stand-by, until the second adsorbent unit reaches breakthrough.

The process continues with flow through the second adsorbent column to generate the second adsorbent unit effluent stream. When the second adsorbent bed is near breakthrough, the pressure in the first adsorbent unit is equalized to the pressure in the second adsorbent unit. The olefins feed stream is switched to the first adsorbent unit, and the first adsorbent unit effluent stream is passed to the second adsorbent unit, displacing the second adsorbent unit fluid. Upon displacing the regenerant in the first adsorbent unit, the passing of the first adsorbent unit effluent stream to the second adsorbent unit is discontinued. The first adsorbent unit effluent stream is now passed to the benzene alkylation unit. The process not completes the cycle by passing the regenerant to the second adsorbent unit to regenerate the second adsorbent unit. The regenerant flows through the second adsorbent unit in the same as the olefins feed stream.

A preferred regenerant is benzene. The regenerant passing from the adsorbent units during regeneration is passed to a regenerant column wherein the contaminated regenerate is separation into an overhead stream comprising regenerant, and a bottoms stream comprising heavy aromatics.

The process can further include the use of a trim adsorbent unit. The trim adsorbent unit is a smaller adsorbent unit and is used to finish up the displacement of the end of an adsorbent unit during the displacement step. At the end of the displacement step, the effluent stream from the adsorbent unit having the fluid displaced from the adsorbent unit is passed to the trim adsorbent unit to adsorb residual heavy aromatics from the adsorbent unit. The effluent from the trim displacement unit is passed to the benzene alkylation unit. After the first, or second, adsorbent unit is placed on line, the trim bed is regenerated with a regenerant.

The process can be seen in the FIGURE, wherein an olefins feedstream 10 is passed to the first adsorbent unit 20 to generate the first adsorbent unit effluent stream 22 having a reduced heavy aromatics content. The effluent stream 22 is passed to the alkylation unit. As the process proceeds and the first adsorbent unit 20 is reaching its capacity, the process begins to prepare the second adsorbent unit 30. This is done by equalizing the pressure between the first and second adsorbent units 20, 30 through the opening of an appropriate valve 32. While the FIGURE is representative, it is not intended to include all potential flows, and as such not all valves may be represented. The adsorbent units reach capacity at breakthrough, or when an analyzer 44, 45 determines that the heavy aromatics content exceeds a predetermined level of tolerance for the olefins stream.

After pressure equalization, the valve 34 to the first adsorbent unit 20 is closed. Other valves are opened, and the fluid inside the second adsorbent unit 30 is passed through a line 40 to the inlet of the first adsorbent unit 20, displacing residual olefins and passing the residual first adsorbent unit effluent 22 to the alkylation unit. When the displacement is finished, the second adsorbent unit 30 is on-line, and the olefins feed stream 10 continues to be passed to the second adsorbent unit 30 to generate a second adsorbent unit effluent stream 36, which is passed to the alkylation unit.

During the operation when the second adsorbent unit 30 is on-line, the first adsorbent unit 20 is regenerated. A regenerant stream 50 is passed to the first adsorbent unit 20 through a branch line 52. The regenerant displaces adsorbed heavy aromatics, and generates a spent regenerant stream 54. The spent regenerant stream 54 is passed to the regenerant column 60 to generate an overhead stream 62 comprising regenerant, and a bottoms stream 64 comprising heavy aromatics. After regeneration of the first adsorbent unit 20, it is placed on stand-by. The regenerant stream 62 is recycled to be reused.

In addition, while the first adsorbent unit 20 is being regenerated, a stream of benzene is passed through the trim adsorbent unit 70 to generate a trim adsorbent unit effluent stream 72. The trim adsorbent unit effluent stream 72 is passed to the alkylation unit.

The cycle continues until the second adsorbent unit 30 reaches breakthrough. The first adsorbent unit 20 is prepared for bringing on-line by equalizing the pressure between the first adsorbent unit 20 and the second adsorbent unit 30. The olefins feed stream 10 is switched to the first adsorbent unit 20 by closing the valve 32 and opening the valve 34. The fluid in the first adsorbent unit 20 is displaced and passed through line 42 to the second adsorbent unit 30.

Following the displacement of the fluid from the second adsorbent unit 30 to the first adsorbent unit 20, a trim displacement of the final, small amount of fluid from the second adsorbent unit 30 is passed through line 56 to the trim adsorbent unit 70, with the trim adsorbent unit effluent stream 72 passed to the alkylation unit. The first adsorbent unit effluent stream 22 is now on-line and passed to the alkylation unit.

The bed on-line and the regeneration step are all done at the same temperature and in the liquid phase. A preferred regeneration temperature is between 110C and 150C, with a preferred regeneration temperature near 130C. A trim bed is done to even out the composition of the steams over the course of the operation. This could also be accomplished by a mixing drum as is the case with the conventional design, but the trim bed will be much smaller that a mixing drum and will be more cost effective.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the removal of heavy aromatics from an olefins stream comprising passing an olefins feed stream to a first adsorbent unit in two unit adsorbent system to generate a first adsorbent effluent stream with reduced heavy aromatics content; running the first adsorbent unit until breakthrough; equalizing pressure in a second adsorbent unit to the pressure of the first adsorbent unit; passing the olefins feed stream to the second adsorbent unit to generate a second adsorbent unit effluent stream with reduced heavy aromatics content; passing the second adsorbent unit effluent stream to the first adsorbent unit, displacing the first adsorbent unit fluid; discontinuing the first adsorbent unit displacement; passing regenerant to the first adsorbent unit to regenerate the first adsorbent unit, wherein the regenerant flows in a co-current direction relative to the olefin feed stream through the first adsorbent unit; equalizing the in the first adsorbent unit to the pressure of the second adsorbent unit; passing the olefins feed stream to the first adsorbent unit to generate the first adsorbent unit effluent stream; passing the first adsorbent unit effluent stream to the second adsorbent unit, displacing the second adsorbent unit fluid; discontinuing the second adsorbent unit displacement; and passing regenerant to the second adsorbent unit to regenerate the second adsorbent unit, wherein the regenerant flows in a co-current direction relative to the olefin feed stream through the first adsorbent unit. An embodiment of the invention is one, any or all of prior embodiments in this paragraph up through the first embodiment in this paragraph further comprising passing the first adsorbent bed effluent stream to a benzene alkylation unit. An embodiment of the invention is one, any or all of prior embodiments in this paragraph up through the first embodiment in this paragraph further comprising passing the second adsorbent bed effluent stream to a benzene alkylation unit. An embodiment of the invention is one, any or all of prior embodiments in this paragraph up through the first embodiment in this paragraph further comprising a trim displacement of the first adsorption unit following the first adsorption unit displacement. An embodiment of the invention is one, any or all of prior embodiments in this paragraph up through the first embodiment in this paragraph wherein the trim displacement is performed with regenerant. An embodiment of the invention is one, any or all of prior embodiments in this paragraph up through the first embodiment in this paragraph further comprising a trim displacement of the second adsorption unit following the second adsorption unit displacement. An embodiment of the invention is one, any or all of prior embodiments in this paragraph up through the first embodiment in this paragraph wherein the trim displacement is performed with regenerant. An embodiment of the invention is one, any or all of prior embodiments in this paragraph up through the first embodiment in this paragraph further comprising putting the first adsorbent unit on standby after passing the regenerant to the first adsorbent unit. An embodiment of the invention is one, any or all of prior embodiments in this paragraph up through the first embodiment in this paragraph further comprising putting the second adsorbent unit on standby after passing the regenerant to the second adsorbent unit. An embodiment of the invention is one, any or all of prior embodiments in this paragraph up through the first embodiment in this paragraph wherein the regenerant is benzene. An embodiment of the invention is one, any or all of prior embodiments in this paragraph up through the first embodiment in this paragraph wherein the heavy aromatics comprise C7 and heavier aromatics. An embodiment of the invention is one, any or all of prior embodiments in this paragraph up through the first embodiment in this paragraph wherein the olefins feed stream is generated by a paraffins dehydrogenation unit. An embodiment of the invention is one, any or all of prior embodiments in this paragraph up through the first embodiment in this paragraph further comprising passing the first adsorbent unit effluent stream to an alkylation unit. An embodiment of the invention is one, any or all of prior embodiments in this paragraph up through the first embodiment in this paragraph further comprising passing the second adsorbent unit effluent stream to an alkylation unit. An embodiment of the invention is one, any or all of prior embodiments in this paragraph up through the first embodiment in this paragraph wherein the alkylation unit is a benzene alkylation unit.

A second embodiment of the invention is a process for the removal of heavy aromatics from an olefins stream comprising passing an olefins feed stream to a first adsorbent unit in two unit adsorbent system to generate a first adsorbent effluent stream with reduced heavy aromatics content; running the first adsorbent unit until breakthrough; equalizing pressure in a second adsorbent unit to the pressure of the first adsorbent unit; passing the olefins feed stream to the second adsorbent unit to generate a second adsorbent unit effluent stream with reduced heavy aromatics content; passing the second adsorbent unit effluent stream to the first adsorbent unit, displacing the first adsorbent unit fluid; discontinuing the first adsorbent unit displacement and moving the first adsorbent unit off-line and the second adsorbent unit on-line; performing a trim displacement of the first adsorption unit following the first adsorption unit displacement; passing regenerant to the first adsorbent unit to regenerate the first adsorbent unit, wherein the regenerant flows in a co-current direction relative to the olefin feed stream through the first adsorbent unit; equalizing the in the first adsorbent unit to the pressure of the second adsorbent unit; pass the olefins feed stream to the first adsorbent unit to generate the first adsorbent unit effluent stream; passing the first adsorbent unit effluent stream to the second adsorbent unit, displacing the second adsorbent unit fluid; discontinuing the second adsorbent unit displacement and moving the second adsorbent unit off-line and the first adsorbent unit on-line; performing a trim displacement of the second adsorption unit following the second adsorption unit displacement; and passing regenerant to the second adsorbent unit to regenerate the second adsorbent unit, wherein the regenerant flows in a co-current direction relative to the olefin feed stream through the first adsorbent unit. An embodiment of the invention is one, any or all of prior embodiments in this paragraph up through the second embodiment in this paragraph further comprising passing the first adsorbent unit effluent stream and the second adsorbent unit effluent stream to an alkylation unit. An embodiment of the invention is one, any or all of prior embodiments in this paragraph up through the second embodiment in this paragraph wherein the regenerant is benzene. An embodiment of the invention is one, any or all of prior embodiments in this paragraph up through the second embodiment in this paragraph wherein the heavy aromatics comprise C7 and heavier aromatics. An embodiment of the invention is one, any or all of prior embodiments in this paragraph up through the second embodiment in this paragraph wherein the trim displacement comprises passing benzene to the adsorbent unit being moved off line.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the removal of heavy aromatics from an olefins stream comprising:
    passing an olefins feed stream to a first adsorbent unit in two unit adsorbent system to generate a first adsorbent effluent stream with reduced heavy aromatics content;
    running the first adsorbent unit until breakthrough;
    equalizing pressure in a second adsorbent unit to the pressure of the first adsorbent unit;
    passing the olefins feed stream to the second adsorbent unit to generate a second adsorbent unit effluent stream with reduced heavy aromatics content;
    passing the second adsorbent unit effluent stream to the first adsorbent unit, displacing the fluid in the first adsorbent unit;
    discontinuing the first adsorbent unit displacement and moving the first adsorbent unit off-line and the second adsorbent unit on-line;
    performing a trim displacement of the first adsorption unit following the first adsorption unit displacement;
    passing regenerant to the first adsorbent unit to regenerate the first adsorbent unit, wherein the regenerant flows in a co-current direction relative to the olefin feed stream through the first adsorbent unit;
    equalizing the in the first adsorbent unit to the pressure of the second adsorbent unit;
    passing the olefins feed stream to the first adsorbent unit to generate the first adsorbent unit effluent stream;
    passing the first adsorbent unit effluent stream to the second adsorbent unit, displacing the fluid in the second adsorbent unit;
    discontinuing the second adsorbent unit displacement and moving the second adsorbent unit off-line and the first adsorbent unit on-line;
    performing a trim displacement of the second adsorption unit following the second adsorption unit displacement; and
    passing regenerant to the second adsorbent unit to regenerate the second adsorbent unit, wherein the regenerant flows in a co-current direction relative to the olefin feed stream through the first adsorbent unit.

2. The process of claim 1 further comprising passing the first adsorbent unit effluent stream and the second adsorbent unit effluent stream to an alkylation unit.

3. The process of claim 1 wherein the regenerant is benzene.

4. The process of claim 1 wherein the heavy aromatics comprise C7 and heavier aromatics.

5. The process of claim 1 wherein the trim displacement comprises passing benzene to the adsorbent unit being moved off line.

* * * * *